United States Patent [19]
DuBose et al.

[11] Patent Number: 5,986,075
[45] Date of Patent: Nov. 16, 1999

[54] PROCESS FOR THE PRODUCTION OF DIAZONIUM COMPOUNDS WITH A LOW CONTENT OF SODIUM IONS

[75] Inventors: John C. DuBose, Summerville; Andrew D. Johnson, Goose Creek; Samuel Shaun Murphree, Summerville, all of S.C.; Edzard Tholema, Odenthal, Germany; Helmut Hoffmann, Leverkusen, Germany; Wolfgang Zarges; Wolfgang Frank, both of Köln, Germany; Bettina Burkhardt, Krefeld, Germany

[73] Assignees: Bayer Corporation, Pittsburgh, Pa.; Bayer Aktiengesellschaft, Leverkusen, Germany

[21] Appl. No.: 09/234,449

[22] Filed: Jan. 20, 1999

[51] Int. Cl.⁶ ............... C07C 245/12; C09B 41/00; D06P 1/02; C09D 11/00
[52] U.S. Cl. ............... 534/558; 534/559; 534/560; 534/582; 534/728; 534/771; 534/772; 8/527; 8/664; 106/31.45; 106/31.48
[58] Field of Search ............... 534/558, 559, 534/560, 887, 582; 252/1; 8/664, 527

[56] References Cited

U.S. PATENT DOCUMENTS

| | | | |
|---|---|---|---|
| 4,500,321 | 2/1985 | Hugelshofer et al. | 8/527 |
| 4,523,924 | 6/1985 | Lacroix | 8/527 |
| 4,838,895 | 6/1989 | Galli et al. | 8/527 |
| 5,565,102 | 10/1996 | Brandt et al. | 210/500.28 |

*Primary Examiner*—Fiona T. Powers
*Attorney, Agent, or Firm*—Joseph C. Gil; Richard E.L. Henderson

[57] ABSTRACT

The present invention relates to a process for desalting aqueous suspensions containing an organic diazonium compound and electrolytes containing Na ions, in which the aqueous suspension is passed through a semipermeable membrane.

11 Claims, No Drawings

PROCESS FOR THE PRODUCTION OF DIAZONIUM COMPOUNDS WITH A LOW CONTENT OF SODIUM IONS

BACKGROUND OF THE INVENTION

The present invention relates to a process for the production of diazonium compounds with a low content of sodium ions and the use of the resulting compounds for the preparation of azo compounds, and in particular azo dyes.

Most dye applications require dyes which are highly soluble in water. Some salt forms of dyes containing sulfo or carboxy groups are for example less water-soluble than others. The corresponding sodium salts or sodium mixed salts, such as for example Na/K salts, frequently have particularly low solubility. Where possible it is therefore desirable to prepare dyes from other salt forms, such as for example lithium, potassium or ammonium salts. Particularly in the case of dye salts of relatively low solubility conversion into the corresponding more highly water-soluble salt forms is very complicated since high dilution rates are required and considerable quantities of effluent result.

Attempts are therefore made to use starting materials which are already in free from or have only a low content of sodium ions in the coupling reaction for the preparation of corresponding azo compounds, and in particular azo dyes.

Diazonium compounds, which are generally obtained by the diazotization of the corresponding amines with sodium nitrite in the presence of inorganic acids, are frequently obtained in the form of water-insoluble compounds which can be filtered off and then washed with water until free of sodium ions. This process is problematical from the point of view of safety, since the filter cake can dry onto the membrane and, on exposure to impact or heat, the explosive decomposition of the diazonium compounds, which are known to be unstable in the dry state, is then likely to occur.

A process has now been found which avoids the above-mentioned disadvantages.

SUMMARY OF THE INVENTION

The process according to the invention relates to the desalination of aqueous suspensions containing at least one diazonium compound and electrolytes containing sodium ions, in which the aqueous suspension is passed through a semipermeable membrane. The compounds can also be in the form of betaines.

DETAILED DESCRIPTION OF THE INVENTION

The preferred diazonium compounds used are aromatic diazonium compounds which particularly preferably contain one or more sulfo and/or carboxy groups. Such diazonium compounds preferably have a water-solubility of less than 5, and in particular less than 1 g/l at 20° C. Preferred counterions are halides, and in particular chloride and sulfate. The compounds can however also be in the form of betaines.

Particularly preferred diazonium compounds are those selected from the group of formulas (I) and (II)

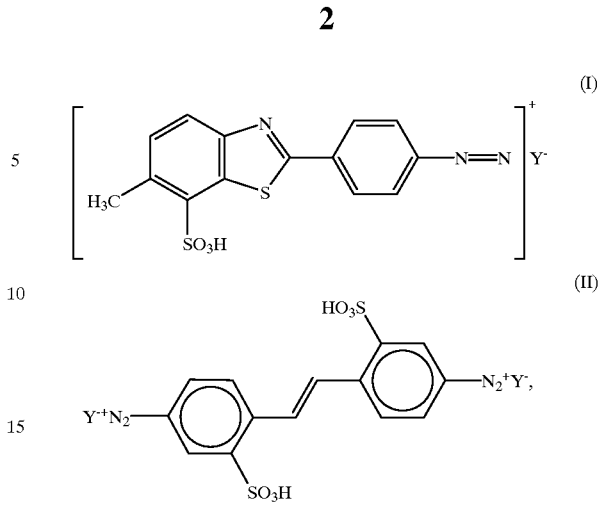

wherein $Y^-$ represents an anion, preferably halide and sulfate, and in particular $Cl^-$ and $(SO^{2-}_4)_{1/2}$, or their betaines.

The suspensions used for the process according to the invention referably have a pH value of 0.5 to 5, and in particular 1 to 3. The membrane desalination is preferably carried out at a temperature of 5 to 70° C., and in particular at 20 to 50° C. In the process according to the invention in particular electrolytes containing sodium ions, such as NaCl, $Na_2SO_4$, $NaHSO_4$, and NaOAc are removed. Preferably any other inorganic electrolytes present are also removed. The aqueous suspensions employed preferably have sodium ion contents of 0.2 to 5.0% by weight. Following the membrane desalination according to the process of the invention the aqueous suspensions have a sodium ion content of preferably less than 0.1%, and preferably less than 0.05%. These percentages preferably also apply to the total content of inorganic electrolytes.

In addition, in the context of the present application a low content of sodium ions or electrolytes is understood to mean a $Na^+$ or electrolyte content of less than 0.1% by weight, based on the suspension.

The aqueous suspensions used in the process according to the invention are preferably reaction suspensions obtained by the reaction of the corresponding amines with alkali nitrite in inorganic acids, preferably hydrochloric acid and/or sulfuric acid.

The semipermeable membranes used in the process according to the invention are preferably produced from inorganic or organic materials. Such materials are for example ceramics or acid-resistant organic polymer materials. The membrane desalination of the process according to the invention is generally carried out by the so-called cross-flow filtration method.

Cross-flow filtration is understood to mean that the product stream flows tangentially over the membrane surface, thus avoiding the formation of surface layers or filter cakes due to the shearing forces generated.

Micro- and ultrafiltration membranes, preferably of a tubular or capillary module design, are used with particular preference in the process according to the invention. Further possible membrane design forms are spiral wound and disc-tube modules.

The membranes are preferably produced from inorganic (e.g. $TiO_2$, $ZrO_2$, $Al_2O_3$) or organic materials, such as for example polypropylene, partially or completely fluorinated polymers, polyhydantoin (cf. U.S. Pat. No. 5,565,102), polysulfone and polyamide. Membranes having a cutoff value of 3,000 to 200,000 daltons, preferably 50,000 to 200,000 daltons, are preferably used. Preferred membranes of this type are ultrafiltration membranes. Membranes which are also preferred have pore sizes of 0.01 to 10 μm, preferably 0.02 to 0.2 μm. Preferred membranes of this type are microfiltration membranes.

The desalination process according to the invention can be carried out either by means of concentration, during which water is removed from the suspension, or by means of diafiltration, in which the quantity of permeate removed via the membrane is replaced by demineralized, deionized water which is free from or has only a low content of sodium.

Preferably the aqueous suspensions of diazonium compounds obtained according to the process of the invention are used in the presence of a preferably sodium-free base for the preparation of an azo compound, and in particular an azo dye. Particularly preferred coupling components which can be used are barbituric acid or its derivatives, acetoacetic acid derivatives and pyrazolones—in particular for the reaction of the diazonium compound of the formula (I) for the preparation of yellow dyes—as well as H-acid and salicyclic acid derivatives, such as for example 3-methyl-2-hydroxybenzoic acid—in particular for the reaction with the diazonium compound of the formula (II) for the preparation of blue+yellow dyes. Preferred sodium-ion-free bases for the preparation of dyes using the desalted aqueous suspensions according to the process of the invention are for example LiOH, KOH, (CH$_3$)$_4$NOH and amines, in particular alkanolamines, such as for example CH$_3$—NH—CH$_2$CH$_2$OH, CH$_3$—N(CH$_2$CH$_2$OH)$_2$, H$_2$N—CH$_2$CH$_2$OH, HN(CH$_2$CH$_2$OH)$_2$, N(CH$_2$CH$_2$OH)$_3$, (CH$_3$CH$_2$)$_2$NCH$_2$CH$_2$OH, N(CH$_2$CH$_2$OCH$_2$CH$_2$OH)$_3$,

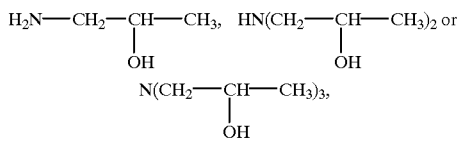

and mixtures thereof. Tertiary amines are particularly preferred. The corresponding dyes are suitable in particular for dyeing cellulose-containing materials, preferably paper, cotton and viscose, and for ink jet printing.

The following examples further illustrate details for the process of this invention. The invention, which is set forth in the foregoing disclosure, is not to be limited either in spirit or scope by these examples. Those skilled in the art will readily understand that known variations of the conditions and processes of the following preparative procedures can be used to prepare these compounds. Unless otherwise noted, all temperatures are degrees Celsius and all percentages are percentages by weight.

EXAMPLES

Example 1

1.00 mole equivalent of dehydrothiotoluidinic acid is reacted with 0.99 mole equivalent of sodium nitrite and 1.65 mole equivalent of hydrochloric acid to form the diazonium ion (I) (Y=Cl$^-$).

72 kg of the above synthesis suspension (pH 1.2; sodium content 2800 ppm; content of diazonium ion 0.13 mole/kg) are subjected to cross-flow ultrafiltration at 18° C. For this purpose a polymer membrane (polyhydantoin on a polyphenylene sulfide support) in the form of a ½" tubular membrane, of the kind disclosed for example in U.S. Pat. No. 5,565,102, is used. The module employed has a total membrane surface area of 0.9 m$^2$ and a length of 1.2 m.

Desalination/Concentration

Beginning with a module inlet pressure of 10 bars, 42 kg of permeate are initially removed before diafiltration is carried out by removing 180 kg of permeate and continuously adding 180 kg of completely demineralized water. For this purpose the module inlet pressure is increased to 20 bars.

Final concentration is carried out by removing 16 kg of permeate. The permeate flow density is initially approx. 230 kg/(m$^2$h) and is still approx. 110 kg/(m$^2$h) in the final concentration step.

The retentate has a sodium content of 90 ppm and a content of the diazonium ion of 0.66 mole/kg.

Coupling Reaction

The resulting diazonium suspension, which has a low content of sodium, is reacted with 0.96 mole equivalents of barbituric acid, 0.17 mole equivalents of LiOH and 0.79 mole equivalents of triethanolamine to form the target dye of the formula (III)

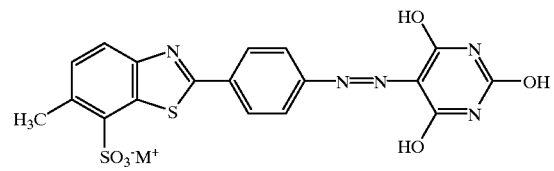

wherein M is Li or HN(CH$_2$CH$_2$OH)$_3$.

Following standardization (diluting with completely demineralized water to the specified dye content and adding the required preservatives) a highly concentrated liquid formulation is obtained which is stable in storage.

Example 2

A ceramic microfiltration membrane can also alternatively be used for the treatment of the diazonium ion suspension (I): A capillary membrane from Membralox (in which ZrO$_2$ is used as the active separating layer) with a pore size of 0.05 μm (channel depth: 6 mm; membrane surface area: 0.9 m$^2$) was operated at a module inlet pressure of 2 bars and a temperature of 45° C.

Following the initial concentration to 60% of the starting volume (approx. 950 l) the total volume is replaced 5.2 times with completely demineralized water until the conductivity of the suspension reaches a value of 500 μS/cm. The sodium content in the retentate is 35 ppm. The average permeate flow density is 185 l/(m$^2$h). The resulting diazonium suspension having a low content of sodium is reacted with cyaniminobarbituric acid and triethanolamine to form the yellow dye of the formula (IV)

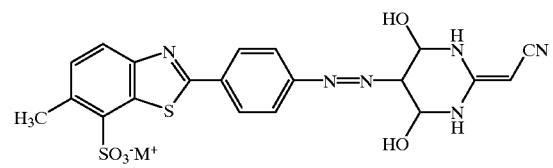

wherein M is Li, HN(CH$_2$CH$_2$OH)$_3$.

Following standardization (adjusting the suspension to the specified dye content and adding the required preservatives) a highly concentrated liquid formulation is obtained which is stable in storage.

What is claimed is:

1. A process for desalting aqueous suspensions containing an organic diazonium compound and electrolytes containing sodium ions comprising passing said aqueous suspension through a semipermeable membrane.

2. A process according to claim 1 wherein the semipermeable membrane is a microfiltration or ultrafiltration membrane.

3. A process according to claim 1 wherein the membrane process is carried out by means of so-called cross-flow filtration.

4. A process according to claim 1 wherein the organic diazonium compounds are compounds of the formulas (I) and (II)

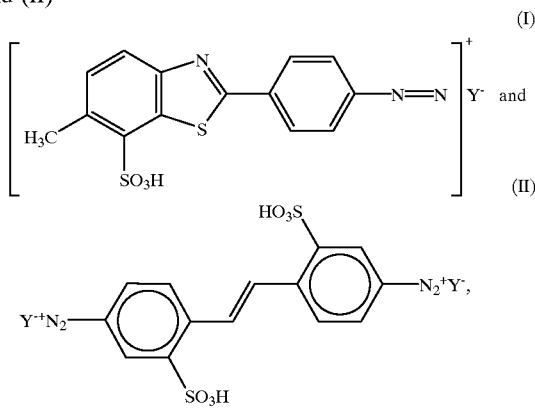

wherein Y⁻ represents an anion, or a betaine thereof.

5. A process according to claim 1 wherein the desalination of the suspension is carried out a pH value of 0.5 to 5.

6. A process according to claim 1 wherein the desalination of the aqueous suspension is carried out at a temperature of 5 to 70° C.

7. A method for preparing an azo compound comprising coupling a desalted organic diazonium compound obtained according to the process of claim 1 with a coupling compound.

8. A method according to claim 7 wherein the coupling reaction is carried out in the presence of one or more organic bases free of sodium ions.

9. A method according to claim 7 wherein the coupling compound is barbituric acid or derivative thereof, acetoacetic acid or an amide thereof, salicylic acid or a derivative thereof, or a naphthalene-sulfonic acid derivative.

10. A dyeing method comprising dyeing a cellulose-containing material with an azo compound prepared according to claim 7.

11. A method for ink jet printing comprising applying an azo compound prepared according to claim 7 to a substrate with an ink jet apparatus.

* * * * *